United States Patent [19]

Knorr et al.

[11] 4,283,545

[45] Aug. 11, 1981

[54] PROCESS FOR THE PREPARATION OF 1,2,4-TRIAZOLE

[75] Inventors: Harald Knorr, Gersthofen; Thomas Maier, Frankfurt am Main; Hilmar Mildenberger, Kelkheim; Helmut Korbanka, Adelsried, all of Fed. Rep. of Germany

[73] Assignee: Hoechst Aktiengesellschaft, Fed. Rep. of Germany

[21] Appl. No.: 199,460

[22] Filed: Oct. 22, 1980

[30] Foreign Application Priority Data

Oct. 26, 1979 [DE] Fed. Rep. of Germany ....... 2943265

[51] Int. Cl.$^3$ ........................................... C07D 249/08
[52] U.S. Cl. .................................................. 548/262
[58] Field of Search ........................................ 548/262

[56] References Cited

FOREIGN PATENT DOCUMENTS 2802491 7/1979 Fed. Rep. of Germany ........... 548/262

OTHER PUBLICATIONS

Ainsworth et al., A. J. Am. Chem. Soc., vol. 77, pp. 621–624, (1955).
Elderfield, Heterocyclic Compounds, vol. 7, (New York, 1961), pp. 433–435.

*Primary Examiner*—Alton D. Rollins
*Attorney, Agent, or Firm*—Connolly & Hutz

[57] ABSTRACT

1,2,4-triazole is obtained by cyclization of N,N'-diformylhydrazine with ammonia in the presence of formamide. The amount of ammonia required is either formed in situ from thermally decomposable ammonium salts, or supplied by feeding in gaseous ammonia. Simultaneously, the water of reaction is constantly distilled off from the system.

4 Claims, No Drawings

PROCESS FOR THE PREPARATION OF 1,2,4-TRIAZOLE 1,2,4-triazole serves as starting material for the manufacture of important fungicidal products.

The above compound is obtained with very good yields by reaction of 1,3,5-triazine with hydrazine hydrochloride [C. J. Grundmann and A. Kreutzberger, J. Amer. Chem. Soc. 79 2839 (1957);id., J. Org. Chem. 21, 1037 (1956); U.S. Pat. No. 2,800,486 (23.07.1957); C.A. 51, 18009 a (1957)]. This process, however, is uneconomic because of the high cost of starting materials, and therefore rather unsuitable for the synthesis of 1,2,4-triazole on an industrial scale. Moreover, the hydrogen chloride which forms must be neutralized, so that large amounts of undesirable salts are formed in addition.

A further method of synthetizing 1,2,4-triazole is the diazotization of 3-amino-1,2,4-triazole, which allows to obtain yields of about 75% (R. A. Henry and W. G. Finnegan, J. Amer. Chem. Soc 76, 290 (1954)). The disadvantages of this process reside in the necessity of increased safety precautions and the risk of formation of nitroso compounds which may have carcinogenic properties.

1,2,4-triazole can be prepared alternatively by reaction of N,N'-diformylhydrazine with excess liquid ammonia in an autoclave at about 200° C. (C. Ainsworth and R. G. Jones, J. Amer. Chem. Soc. 77, 621 (1955)). 1,2,4-triazole is thus obtained with a yield of from 70 to 80%.

The disadvantages of this process are the following: on the one hand, operations have to be carried out in a closed system under high pressure, and on the other hand, a large excess of ammonia (20 mols), moreover in liquid form, is required in order to obtain the above yields. The excess ammonia is let off after termination of the reaction, and must normally be condensed again. Furthermore, work-up involves a treatment with hot ethyl acetate, and in the case where the reaction is to be carried out on a large scale, this solvent, too, has to be regenerated and stored.

The same reference hints to a possibility of preparing 1,2,4-triazole from hydrazine, formamide and ammonia with similar yields also in an autoclave. This process, however, has the same drawbacks as described above, because the sole difference of preparation resides in the fact that N,N'-diformylhydrazine is not isolated but directly reacted further.

Other processes of 1,2,4-triazole synthesis are less interesting because of their low yields [G. Pellizzari, Gazz. chim. ital. 24, 222 (1894); id. Ber. 27 R, 801 (1894); G. Pellizzari and C. Massa, Atti accad. Lincei (5) 10 I, 363 (1901); H. H. Strain, J. Amer. Chem. Soc. 49, 1996 (1927)].

It was therefore the object of the invention to find a process for the preparation of 1,2,4-triazole, which allows to obtain this compound with high yields although operating without pressure and requiring small amounts of ammonia only.

Surprisingly, this object is achieved by reaction of N,N'-diformylhydrazine in formamide at elevated temperatures with ammonia which is either supplied from a compound splitting off ammonia directly in the reaction mixture, or introduced into it.

The invention provides therefore an improved process for the preparation of 1,2,4-triazole by cyclization of N,N'-diformylhydrazine in the presence of ammonia at elevated temperature, which comprises supplying the amount of ammonia required either (a) by forming it in situ from ammonium carbonate or ammonium hydrogen carbonate with heating to 150°–250° C., or (b) introducing gaseous ammonia into the N,N'-diformylhydrazine under the same conditions, while operating in both cases without pressure and in formamide as solvent, and constantly distilling off the water formed.

It was not to be expected that 1,2,4-triazole could be obtained according to this operation mode, let alone with yields of more than 80%, because in compliance with the teaching of Ainsworth and Jones (loc. cit.) also in this case application of a large ammonia excess combined with high pressure seemed to hold the only promise of success. Moreover, it was not to be expected at all that such yields are attained with the use of amounts of ammonium carbonate, ammonium hydrogen carbonate or gaseous ammonia which are only equivalent (relative to the ammonia content) to the N,N'-diformylhydrazine. For, it had to be expected that under these operational conditions the water of reaction formed would adversely effect the course of the reaction because, as own tests had proved, diformylhydrazine is decomposed on heating in the presence of water or reacts with aqueous ammonia only insufficiently.

The amount of ammonium carbonate or ammonium hydrogen carbonate to be used must be chosen in such a manner that per mol of N,N'-diformylhydrazine the equivalent to 5 times equivalent amount of ammonium is present; 1 to 3 equivalents being preferred. When gaseous ammonia is used, its amount is likewise from 1 to 5 equivalents, preferably, however, 1 to 2 equivalents.

The reaction is carried out at a temperature of from 150 to 250, preferably 160° to 200° C.

N,N'-diformylhydrazine can be prepared according to the instructions of Ainsworth and Jones (loc. cit.) It has the following structure:

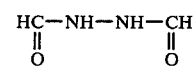

There are no special requirements as to the further starting materials, that is, the solvent, formamide, used in a 2- to 10-fold weight amount relative to N,N'-diformylhydrazine, and the ammonium carbonate, ammonium hydrogen carbonate or gaseous ammonia.

In the case of operating according to variant (a) with ammonia formed in situ, the details of synthesis are preferably the following: a mixture of N,N'-diformylhydrazine and the carbonate in question in substance or in the form of a suspension is added portionwise to formamide having a temperature of from 150° to 250° C., and reacted correspondingly. Alternatively, a N,N'-diformylhydrazine/ammonium carbonate/formamide suspension is passed through heated zones. The $CO_2$ set free in this reaction escapes together with the water of reaction and a certain amount of solvent; the two latter substances being separated in a condenser. For work-up of the reaction mixture, first the formamide is distilled off under reduced pressure, and the 1,2,4-triazole of the formula

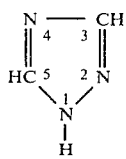

is then obtained by vacuum distillation.

In the cyclization according to variant (b), the reaction is preferably carried out in cylindrical reactors or columns. In the case of batchwise operation, for example, a solution of N,N'-diformylhydrazine in formamide is introduced into the reactor, and gaseous ammonia is fed in at temperatures of from 150° to 250° C. with vigorous agitation of the reaction mixture, for example by stirring or other physical means such as vibration, while simultaneously the water of reaction which forms escapes as a mixture with formamide. A continuous process may be carried out for example as follows: the solution of N,N'-diformylhydrazine in formamide trickles through the packing of a heated column, while simultaneously gaseous ammonia is fed in in parallel current or countercurrent. Alternatively, the operations may be carried out in a flooded column to which a N,N'-diformylhydrazine/formamide mixture is fed continuously, while simultaneously the reaction product is removed continuously, too.

The following examples illustrate the invention.

EXAMPLE 1

280 ml of formamide are introduced into a flask provided with agitator and distillation column on top, and heated to 180° C. A mixture of 2.4 mols of ammonium carbonate (216.4 g) and 1.2 mols (105.6 g) of N,N'-diformylhydrazine is added portionwise in such a manner that the inner temperature does not decrease below 170° C. Simultaneously, water and formamide are distilled off (102.6 g), while $CO_2$ and excess $NH_3$ escape. The reaction being complete, first the formamide and then the 1,2,4-triazole is distilled off in a water jet vacuum. Yield: 90.1% having a melting point of 116° C. (lit.: 120° C.).

EXAMPLE 2

Operations are as in Example 1, but only half the amount of ammonium carbonate (=108.2 g or 1.2 mols) is used. 80.7 g of water and formamide are distilled off. The reaction being complete, work-up is as described above. Yield: 89.3% of 1,2,4-triazole, m.p. 116° C.

EXAMPLE 3

According to the operation mode of Example 1, 280 ml of formamide are heated to 170° C., and a mixture of 1.2 mols of N,N'-diformylhydrazine and 1.2 mols (94.8 g) of ammonium hydrogen carbonate is added. 16.9 g of water and formamide are distilled off. Yield: 89.9% of 1,2,4-triazole, m.p. 116° C.

EXAMPLE 4

Operations are as in Example 3 with the use of 189.6 g (2.4 mols) of ammonium hydrogen carbonate. 46.3 g of water and formamide are distilled off. Yield: 78.6 g (95%) of 1,2,4-triazole, m.p. 116°–120° C.

EXAMPLE 5

Operations are as in Example 1, but only 100 ml of formamide are introduced into the reactor, and a suspension of the reactants in 300 ml of formamide are added so slowly that the inner temperature does not decrease below 170° C. Yield: 77 g of 1,2,4-triazole, m.p. 116°–120° C.

EXAMPLE 6

85 g of a solution of N,N'-diformylhydrazine in formamide (per mol of N,N'-diformylhydrazine 375 g of formamide) are made to trickle through a heatable column packed with Raschig rings having a length of 0.5 m and a diameter of 4 cm and a jacket temperature of 180° C. Simultaneously, 0.5 mol of gaseous ammonia are fed in per hour at the bottom. The water formed in the reaction, together with some formamide, constantly distills off via a descending cooler at the top of the column. The test is stopped after 6 hours, after which period of time 20.4 g of condensate were separated. Subsequently, the formamide and then the triazole are distilled off from the reaction mixture under reduced pressure. Yield of triazole: 71.4 g (86.3% of th.)

EXAMPLE 7

240 ml of formamide are introduced into a heatable bubble-cap column having a length of 0.5 m and a diameter of 4 cm as well as an inner temperature of 170° C. Subsequently, a solution of 105.6 g of N,N'-diformylhydrazine (1.2 mols) in 240 ml of formamide is fed in from above within 2 hours ½, and simultaneously, 1.4 mols of ammonia in gaseous form are fed in at the bottom, while water distils off at the top of the column. The amount of reaction sulution let off and the amount of mixture fed in must be identical. The reaction being complete, the reactor is flushed with $N_2$, the column is emptied and the product is subjected to vacuum distillation in which first the formamide and then the triazole distils off. Yield: 74.7 g of triazole (90.3% of th.).

EXAMPLE 8

A solution of 1.2 mols of N,N'-diformylhydrazine in 240 ml of formamide is introduced at 180° C. (inner temperature) into the column described in Example 7, and about 1.4 mols of gaseous ammonia are fed in within 2 hours at the bottom, while water distils off in admixture with formamide (63.9 g). The reaction being complete, the reactor is flushed with $N_2$, and its contents are let off. The reaction mixture is then worked up as described. Yield: 78.9 g of triazole (95.3% of th.).

EXAMPLE 9

Operations are as in Example 8, and 2.6 mols of gaseous ammonia are fed in within 4 hours. 79.4 g (95.7% of th.) of triazole are obtained.

EXAMPLE 10

A solution of 880 g of N,N'-diformylhydrazine (10 mols) in 3,400 g of formamide is vigorously stirred at an inner temperature of 170° C. in a heatable upright standing cylindrical reactor having a capacity of 10 liters and being provided with an agitator having along its length several blades and paddles. Simultaneously, 14.1 mols of gaseous ammonia are fed in at the bottom within 3 hours ½, while water in admixture with formamide distils off (453.7 g of distillate). The reaction being complete, the reactor is flushed with $N_2$ and then emptied. The reaction mixture is distilled under reduced pressure, while a small amount of a mixture of water and formamide passes over first, then formamide and finally triazole. Yield of triazole: 634 g (91.9% of th.).

EXAMPLE 11

A mixture of 423 g (4.8 mols) of N,N'-diformylhydrazine and 720 g of formamide is introduced into the apparatus of Example 1, and heated to 170°–175° C. Within 6 hours, 758 g (9.6 mols) of $NH_4HCO_3$ are added portionwise in such a manner that the inner temperature does not descrease below 165° C. A mixture of water and formamide is distilled off, while $CO_2$ and excess $NH_3$ escape. Work-up is as described in Example 1, and the triazole is then distilled off in a water jet vacuum.

Yield: 298 g (90%), m.p. 116°–120° C.

What is claimed is:

1. A process for the preparation of 1,2,4-triazole by cyclization of N,N'-diformylhydrazine in the presence of ammonia at elevated temperature, which comprises supplying the amount of ammonia required either (a) by forming it in situ from ammonium carbonate or ammonium hydrogen carbonate with heating to 150°–250° C., or (b) introducing gaseous ammonia into the N,N'-diformylhydrazine under the same conditions, while operating in both cases without pressure and in formamide as solvent, and constantly distilling off the water formed.

2. The process of claim 1, wherein the amount of ammonium carbonate, ammonium hydrogen carbonate or gaseous ammonia corresponds to 1 to 5 equivalents of $NH_3$ per mol of N,N'-diformylhydrazine.

3. The process of claim 1, variant (a), which comprises ($\alpha$) either introducing a mixture of N,N'-diformylhydrazine and ammonium carbonate or ammonium hydrogen carbonate, or a suspension of this mixture in formamide, into formamide heated to 150° to 250° C., or ($\beta$) adding the ammonium carbonate or ammonium hydrogen carbonate, optionally in the form of a suspension in formamide, to a mixture of N,N'-diformylhydrazine and formamide heated to 150° to 250° C.

4. The process of claim 1, variant (b), which comprises feeding instead of ammonium carbonate or hydrogen carbonate gaseous ammonia to a mixture of N,N'-diformylhydrazine and formamide at 150° to 250° C.

* * * * *